United States Patent
Monbaliu et al.

(10) Patent No.: US 11,180,434 B2
(45) Date of Patent: Nov. 23, 2021

(54) PROCESS FOR THE PRODUCTION OF ALLYL COMPOUNDS BY DEOXYDEHYDRATION OF GLYCEROL

(71) Applicant: UNIVERSITÉ DE LIÈGE, Liège (BE)

(72) Inventors: Jean-Christophe Monbaliu, Esneux (BE); Nelly Ntumba Tshibalonza, Liege (BE)

(73) Assignee: UNIVERSITE DE LIEGE, Liege (BE)

( * ) Notice: Subject to any disclaimer, the term of this patent is extended or adjusted under 35 U.S.C. 154(b) by 136 days.

(21) Appl. No.: 16/490,356

(22) PCT Filed: Feb. 26, 2018

(86) PCT No.: PCT/EP2018/054695
§ 371 (c)(1),
(2) Date: Oct. 16, 2019

(87) PCT Pub. No.: WO2018/158198
PCT Pub. Date: Sep. 7, 2018

(65) Prior Publication Data
US 2020/0071248 A1    Mar. 5, 2020

(30) Foreign Application Priority Data
Mar. 3, 2017    (EP) .................................... 17159230

(51) Int. Cl.
*C07C 29/60*    (2006.01)
(52) U.S. Cl.
CPC .................................. *C07C 29/60* (2013.01)
(58) Field of Classification Search
CPC .................................................... C07C 29/30
(Continued)

(56) References Cited

U.S. PATENT DOCUMENTS

2015/0246861 A1    9/2015    Kim et al.
2016/0115109 A1    4/2016    Lee et al.

FOREIGN PATENT DOCUMENTS

EP    3 015 446 A1    5/2016
EP    3 015 447 A1    5/2016
(Continued)

OTHER PUBLICATIONS

Gizelle Sanchez et al: vol. 4, No. 9, May 28, 2014, p. 3090, (Year: 2014).*
(Continued)

*Primary Examiner* — Deborah D Carr
(74) *Attorney, Agent, or Firm* — Blue Filament Law PLLC (57) ABSTRACT

A continuous-flow process for the production of allyl compounds by deoxydehydration of glycerol includes:
  (a) Forming a reactive solution by mixing glycerol (1) with:
    a carboxylic acid (2), and/or
    a triethyl orthoester, preferably triethyl orthoformate (TEOF);
  (b) Feeding the reactive solution to an inlet of a channel of a thermolysis microreactor module wherein the channel has an inner hydraulic diameter, D=4 A/P, wherein A is the area and P the perimeter of a cross-section of the channel, of not more than 1000 μm,
  (c) Exposing the reactive solution to thermolysis by driving a flow of the reactive solution along the channel from the inlet to an outlet, for a thermolysis time, t, at a pressure, P, and at a thermolysis temperature, T, larger than 200° C., to form thermolysis products including at least one allyl compound; and
(Continued)

Recovering the thermolysis products at the outlet and separating the at least one allyl compound from the other thermolysis products.

20 Claims, 5 Drawing Sheets

(58) Field of Classification Search
USPC .......................................................... 568/903
See application file for complete search history.

(56) References Cited

FOREIGN PATENT DOCUMENTS

| EP | 3015446 A1 * | 5/2016 | ............. C07C 29/60 |
|---|---|---|---|
| WO | 2008/092115 A1 | 7/2008 | |

OTHER PUBLICATIONS

Gizelle Sanchez et al: "Catalytic conversion of glycerol to allyl alcohol; effect of a sacrificial reductant on the product yield", Catalysis Science & Technology, vol. 4, No. 9, May 28, 2014 (May 28, 2014), p. 3090, XP055359789, United Kingdom ISSN: 2044-4753, DOI: 10.1039/C4CY00407H * the whole document *.

Xiukai Li et al: "Highly Efficient Process for the Conversion of Glycerol to Acrylic Acid via Gas Phase Catalytic Oxidation of an Allyl Alcohol Intermediate", ACS Catalysis, vol. 6, No. 1, Jan. 4, 2016 (Jan. 4, 2016), pp. 143-150, XP055321214, US ISSN: 2155-5435, DOI:10.1021/acscatal.5b01843 * Scheme *.

Chai et al: "Sustainable production of acrolein: Gas-phase dehydration of glycerol over Nb"20"5 catalyst", Journal of Catalysis, Academic Press, Duluth, MN, US, vol. 250, No. 2,Aug. 14, 2007 (Aug. 14, 2007), pp. 342-349, XP022200532, ISSN: 0021-9517, DOI: 10.1016/J.JCAT.2007.06.016 * 3.6 on p. 77 *.

Atia H et al: "Dehydration of glycerol in gas phase using heteropolyacid catalysts as active compounds", Journal of Catalysis, Academic Press, Duluth, MN, US, vol. 258, No. 1,Aug. 15, 2008 (Aug. 15, 2008), pp. 71-82, XP023181278, ISSN: 0021-9517, DOI: 10.1016/J.JCAT.2008.05.027 * the whole document *.

Yong Liu et al: "From glycerol to allyl alcohol: iron oxide catalyzed dehydration and consecutive hydrogen transfer", Chemical Communications, vol. 46, No. 8, Jan. 1, 2010 (Jan. 1, 2010), p. 1238, XP055054265, ISSN 1359-7345, DOI: 10.1039/b921648k * the whole document *.

Camille Boucher-Jacobs et al: "Catalytic Deoxydehydration of Glycols with Alcohol Reductants", CHEMSUSCHEM, vol. 6, No. 4, Mar. 26, 2013 (Mar. 26, 2013), pp. 597-599, XP055193503, ISSN 1864-5631, DOI: 10.1002/cssc.201200781 * the whole document *.

European Search Report dated Mar. 27, 2017 for European Application No. 17159230.

* cited by examiner

PROCESS FOR THE PRODUCTION OF ALLYL COMPOUNDS BY DEOXYDEHYDRATION OF GLYCEROL

FIELD OF THE INVENTION

The present invention generally relates to the production of allyl compounds, such as allyl alcohol and allyl alkaloates, such as allyl formate. In particular, it concerns a particularly efficient continuous flow process for the production of such allyl compounds which is very efficient, with yields of up to over 95%, at high rate and at moderate to relatively low temperature and pressure.

BACKGROUND OF THE INVENTION

Figure 1:
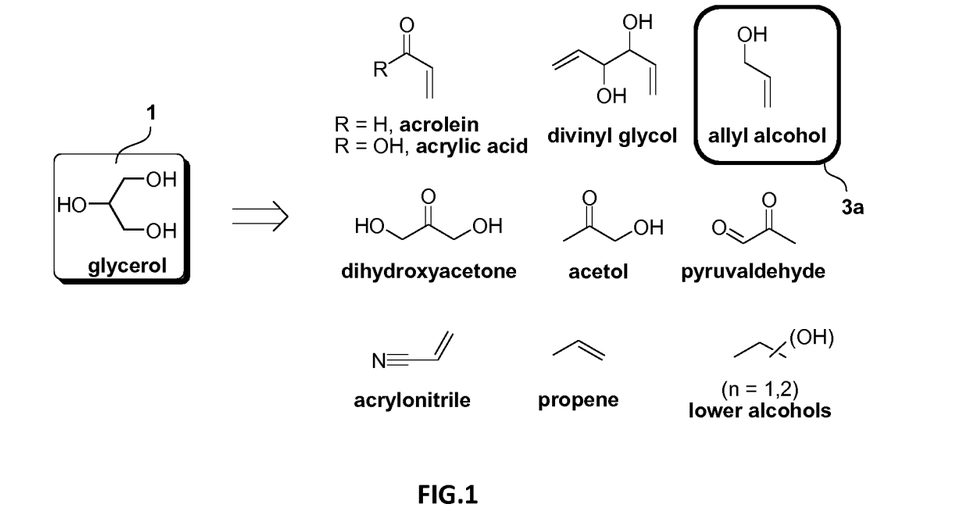
FIG. 1: shows the transformations of glycerol into a selection of important building blocks.

In the actual context of transitioning from an exclusively petro-based to an alternative bio-based chemical industry, glycerol (1,2,3-propanetriol) is a biomass-derived platform molecule with a bright forecast for industrial valorization. Not only is glycerol widely available as a side-product of the ever-increasing biodiesel industry, but it can also be converted into a large palette of important industrial building blocks as illustrated in FIG. 1.

Due to its unique structural features, chemoselective transformations can indeed lead to a variety of chemical functions according to redox processes, dehydration, esterification and etherification reactions, or a combination of the aforementioned, with applications ranging from fine to bulk chemicals. Extensive research efforts for transforming glycerol to important building blocks such as acrolein, acrylic acid, divinyl glycol, allyl alcohol, dihydroxyacetone, acetol, pyruvaldehyde, lactic acid, acrylonitrile, propene, and lower alcohols have been carried out in the last few years. Most of the research dedicated to upgrading glycerol uses a variety of solid catalysts including metal oxides, zeolites, and heteropolyacids at high temperature. Rapid catalyst deactivation by coke deposition (glycerol charring) is often reported as a result of the combination of elevated process temperature and the acidic nature of the catalyst. The present invention focuses on the production of allyl compounds by deoxydehydration (DODH) of glycerol.

Figure 2:
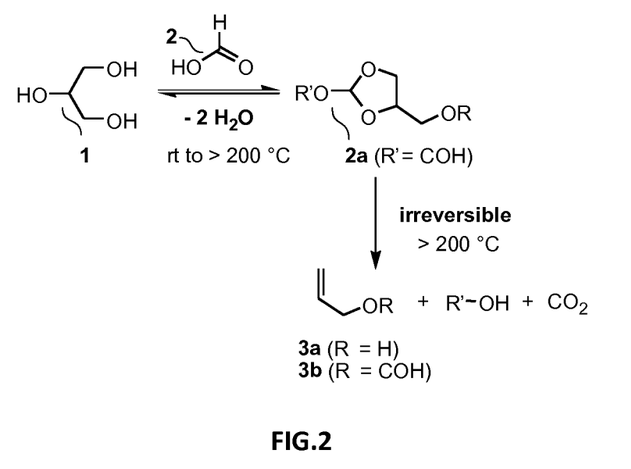
FIG. 2: shows the DODH reaction of glycerol with methanoic acid.

As illustrated in FIG. 2, the deoxydehydration (DODH) is a chemical transformation in which two adjacent hydroxyl functions are converted into an olefin. The DODH of glycerol has emerged as an economically viable and bio-based alternative for the preparation of allyl compounds such as allyl esters and allyl alcohol, the latter being a high value-added chemical synthon. Either metal-catalyzed or methanoic acid-assisted DODH strategies have been reported in the literature as described e.g., in WO200892115, US2015246861, US2016115109. The processes described in said documents use classical macroscopic batch equipment. More recently, Zhang reported reactive distillation CSTR-like process starting from glycerol and methanoic acid at 235° C. [ACS Catalysis, 2016, vol 6, p143]. The reaction products (water, unreacted methanoic acid and allyl alcohol) were distilled continuously off the system and collected by condensation (5.5 g/h output with 99% conversion). The main limitation of the technique is inherently related to the thermal instability of methanoic acid, hence requiring a large excess or sequential addition strategies. The impurity profile of the reaction ultimately depends on two critical process parameters: temperature and reaction time.

Continuous-flow manufacturing, i.e. the transformation of chemicals in micro- or mesofluidic continuous-flow reactors (μ/mFRs), has emerged over the last decade as a powerful alternative to classical macroscopic batch chemical processing (cf. e.g., EP patent application EP16206775). The inherent properties of μ/mFRs come with multiple assets for performing chemical transformations: accurate control over local process parameters, inherent safety, production homogeneity and seamless scale-up. Cleaner and faster chemical processes are designed in μ/mFRs, even under intensified conditions. It is nowadays generally admitted that the implementation of chemical processing in μ/mFRs enables the design of sustainable and greener processes. Continuous-flow strategies dealing with the transformation of bio-sourced platform molecules has drastically increased over the last few years, and the upgrading of glycerol is no exception.

The transformation of glycerol in micro- or mesofluidic continuous-flow reactors (μ/mFRs) is, however, impaired by the high viscosity of glycerol, which cannot flow at a satisfactory rate in capillary channels of diameter less than 1000 μm when driven by a moderate to low pressure at a moderate to low temperature. In order to reduce the viscosity of glycerol, the reaction temperature can be raised, but this increases the cost of production, and limits the choice of materials of the p/mFRs. Alternatively, glycerol can be diluted in water or any other solvent, but the use of glycerol solutions substantially reduces the conversion yield, and the presence of water shifts the reaction balance in the wrong direction. For example, Sánchez et al. describes in Catal. Sci. Technol., 2014, vol 4, p 3090, an implementation of the latter solution, wherein glycerol is diluted to 35% in an aqueous solution to run the DODH of glycerol towards allyl alcohol under continuous-flow conditions over an iron catalyst packed in a mesofluidic device. The yield was, however, quite disappointing, merely reaching 19.5% with a low selectivity.

The present invention proposes a process for producing allyl compounds from glycerol which is highly efficient, requiring simple and inexpensive equipment, and running at moderate to low temperature and pressure. The present invention solves the problem of glycerol high viscosity without the drawbacks associated with raising the reaction temperature or dissolving glycerol in water or any other non-reactive solvent, as discussed supra. The allyl compounds thus produced are allyl alcohol alone or together with allyl formate. These and other advantages of the present invention are presented in continuation

SUMMARY OF THE INVENTION

The present invention is defined by the attached independent claims. The dependent claims define preferred embodiments. In particular, the present invention concerns a continuous-flow process for the production of allyl compounds by deoxydehydration of glycerol comprising the following steps:

(a) Forming a reactive solution by mixing glycerol with:

a carboxylic acid, and/or a triethyl orthoester, preferably triethyl orthoformate (TEOF);

(b) Feeding the reactive solution to an inlet of a channel of a thermolysis microreactor module wherein the channel has an inner hydraulic diameter, D=4 A/P, wherein A is the area and P the perimeter of a cross-section of the channel, of not more than 1000 μm, (c) Exposing the reactive solution to thermolysis by driving a flow of the reactive solution along the channel from the inlet to an outlet, for a thermolysis time, t, at a pressure, P, and at a thermolysis temperature, T, larger than 200° C., to form thermolysis products including at least one allyl compound; and (d) Recovering the thermolysis products at the outlet and separating the at least one allyl compound from the other thermolysis products.

The reactive solution formed in step (a) defined supra, solves the problem of glycerol high viscosity without the drawbacks of raising the reaction temperature or dissolving glycerol in water or any other non-reactive solvent, as discussed in the Background of the invention. The reactive solution has a sufficiently low viscosity for flowing at a satisfactory rate through channels of a μ/mFR, whilst maintaining a high conversion rate at moderate reaction temperatures.

In a preferred embodiment,
the triethyl orthoester is present in the reactive solution in an amount comprised between 1 and 3, preferably between 1.5 and 2.5 equivalents, and is preferably triethyl orthoformate (TEOF), and/or
the carboxylic acid (2) is present in the reactive solution in an amount comprised between 1 and 3, preferably between 1.5 and 2.5 equivalents.

In an alternative embodiment,
the triethyl orthoester is present in the reactive solution in an amount comprised between 1 and 3 equivalent, and is preferably triethyl orthoformate (TEOF), and
the carboxylic acid (2) is present in the reactive solution in an amount comprised between 0.001 and 1.5 equivalent, preferably between 0.01 and 1 equivalent.

The at least one allyl compound present in the thermolysis products may comprise allyl alcohol and allyl formate. The 3a/3b ratio defined as the relative content of allyl alcohol with respect to the total content of allyl compounds present in the thermolysis products (=allyl alcohol/(allyl alcohol+allyl formate)) is comprised between 50 and 100%, preferably between 75 and 99%.

The viscosity of the reactive solution must be sufficiently low to allow flow through a capillary channel to be driven by a moderate pressure gradient. The viscosity, η, of the reactive solution when it is fed to the inlet of the channel is therefore preferably comprised between 0.003 and 1.1 Pa·s, measured by strain-controlled rheology at a temperature of 20° C. and a shear rate of 99.8 $s^{-1}$.

The carboxylic acid preferably has 1 to 5 carbons. It is preferably methanoic acid when used in the absence of a triethyl orthoester, and it is preferably methanoic acid (2m) or ethanoic acid (2e) when used together with a triethyl orthoester.

The thermolysis reaction is preferably carried out at a pressure, P, comprised between 10-75 bar (=145-1088 psi). The thermolysis time, t, is preferably comprised between 0.1 and 15 min. The thermolysis temperature, T, is preferably comprised between 200 and 370° C., preferably between 220 and 320° C.

In a preferred embodiment,
the reactive solution comprises both triethyl orthoformate (TEOF) and a carboxylic acid, present in amounts which do not differ from one another by more than ±20%, said amounts being preferably comprised between 2 and 3 equivalent, preferably between 2.3 and 2.7 equivalent, and wherein
the thermolysis temperature is comprised between 200 and 370° C., preferably between 220 and 320° C.

The present invention also concerns an allyl production line comprising:
(a) sources of reactants including:
a source of glycerol, and
a source of a triethyl orthoester, preferably triethyl orthoformate, and/or a source of carboxylic acid,
(b) a solution tank in fluid communication with the sources of reactants,
(c) a pump bringing in fluid communication the solution tank with a thermolysis microreactor module, wherein
(d) the thermolysis microreactor module comprises:
a channel extending from an inlet to an outlet located downstream from the inlet, said channel having an inner hydraulic diameter, D=4A/P, wherein A is the area and P the perimeter of a cross-section of the channel, of not more than 1000 μm, wherein the pump is located directly upstream of the inlet,
a heating module arranged for heating the channel at a thermolysis temperature of at least 200° C.,
(e) a separating module (61) located downstream of the outlet for separating at least one allyl compound from other thermolysis products.

BRIEF DESCRIPTION OF THE FIGURES

Various embodiments of the present invention are illustrated in the attached Figures.

DETAILED DESCRIPTION OF THE INVENTION

Allyl Continuous Flow Production Line

Figure 4:
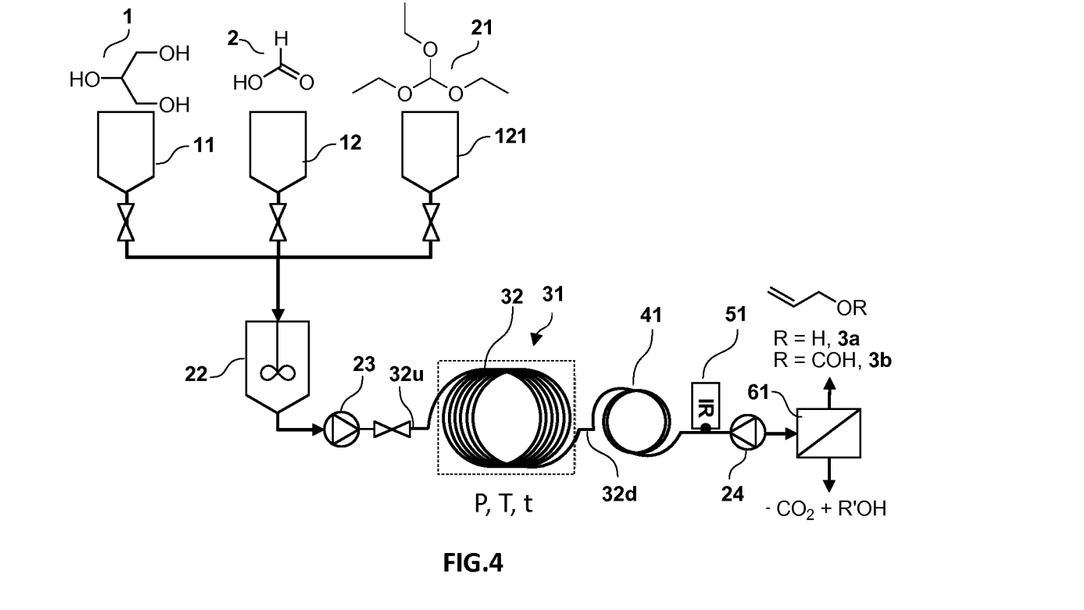
FIG. 4: shows a continuous microreactor module suitable for carrying out the process of the present invention.

As can be seen in FIG. 4, the various steps of a continuous-flow process for the production of an allyl compound by deoxydehydration of glycerol according to the present invention can be carried out in an allyl production line comprising the following components.

The production line must comprise sources of reactants including:
- a source (11) of glycerol (1),
- a source (12) of carboxylic acid (2), and/or a source (121) of a triethyl orthoester (21), preferably triethyl orthoformate (TEOF),
- optionally a source of other additives, such as a solvent (not illustrated and, in most cases, it is not required and it is preferred not to use a solvent or other additives).

The various sources may be provided with valves or volumetric pumps for controlling the flowrate of the various components from the corresponding sources to a solution tank (22). For example, piston pumps (or syringes) can be used to accurately control the flow of each reactant into the solution tank. The valves or volumetric pumps can be controlled by a controlling unit (not shown).

A reactive solution is formed in the solution tank (22) composed of the reactants supplied from the sources of reactants. In all cases the reactive solution comprises glycerol (1) and one or more additives including a triethyl orthoester (121), preferably triethyl orthoformate (TEOF), and/or carboxylic acid (2), preferably methanoic acid. The solution tank can be provided with a stirrer for enhancing homogeneity of the reactive solution. It may also be provided with heating means for heating the reactive solution, for example for lowering the viscosity of the reactive solution.

The solution tank (22) is in fluid communication with a pump (23) for injecting under pressure the reactive solution into an inlet (32u) of a channel (32) extending from said inlet to an outlet (32d) located downstream from the inlet. For example, a HPLC pump can be used to inject the reactive solution into the channel (e.g., Thales Nano Micro-HPLC). Pressures of up to 75 bar (=1088 psi) can be used for the thermolysis of the reactive solution, but the microreactor of the present invention allows excellent yields at much lower pressures comprised between 10 and 25 bar (=145 to 363 psi), preferably between 14 to 20 bar (=203 to 290 psi), more preferably at a pressure of 17±2 bar (=250±29 psi).

The channel (32) forms a capillary defined by a closed perimeter, P, and can be formed by a tube or by a recess in a plate. The reaction is carried out in a microreactor, and the channel has an inner hydraulic diameter, D=4 A/P, of not more than 1000 µm, wherein A is the area and P the perimeter of a cross-section of the channel. The inner hydraulic diameter of the channel can be lower than 1000 µm, such as not more than 750 µm, or not more than 500 µm, and even not more than 250 µm. A channel of inner hydraulic diameter, D, greater than 1000 µm significantly reduces the allyl conversion by thermolysis reaction. This is probably a consequence of temperature gradients across the section of the reactor channel. The channel can be equipped with a backpressure regulator (BPR) (24), which is inserted downstream to enable pressurized operation. Depending on the thermolysis temperature and type of heating module used, the channel can be made of stainless steel, preferably passivated stainless steel, aluminium, copper, PEEK, PEKK, PTFE, ceramics such as silicon carbide, and the like.

The channel comprises a central portion comprised between the inlet and the outlet. If the channel is formed by a tube, the central portion preferably forms one or more coils. If it is formed by a recess in a plate, the recess may meander over the surface of the plate to form a serpentine. The inner walls of the channel can include specific structures, for instance to achieve high mixing. These configurations allow large linear lengths of channel to be housed in a small volume, thus saving space. The central portion of the channel is part of a thermolysis microreactor module (31) comprising a heating module arranged for heating the channel at a thermolysis temperature of at least 200° C. The heating module can be a furnace of any type known in the art allowing the heating of the channel at said temperature and enclosing the central portion of the channel. For example, the heating module can be a conventional electric or gas furnace, or can heat the channel by radiation, such as IR, by induction, by Joule effect, and the like. The heating module must be suitable for heating the interior of the channel to a temperature of at least 200° C., preferably comprised between 200 and 370° C., preferably between 220 and 320° C. If the reaction channel is formed by a recess in a plate, the heating module can also be integrated to the plate as a second recess independent of the channel (32), in which a thermofluid is circulated. The heating module can also be a heating cartridge hosted in the plate. Any heating means known in the art allowing the heating of the reaction mixture within a channel can be applied without affecting the present invention.

By controlling the pressure (and back pressure) in the channel, and depending on the inner hydraulic diameter, D, of the channel the thermolysis time, t, can be controlled. The thermolysis time, t, is preferably comprised between 0.1 and 15 min, more preferably between 1 and 10 min, most preferably between 5 and 8 min. Longer thermolysis times do not significantly increase the yield in allyl compounds. In some cases, in particular at high temperatures, the yield drops with longer thermolysis times because of degradation of some of the components.

In order to control and build up a pressure inside the channel, a backpressure regulator (BPR) (24) can be positioned downstream of the channel. The BPR can be a restriction in the channel cross-section, variable or not, or it can actively generate a counter-pressure. In the latter case, the back pressure, $P_{24}$, generated by the BPR (24) must be lower than the pressure, $P_{23}$, generated by the pump (23) ($P_{24} < P_{23}$), and both pressure and back pressure can be varied to allow the reactive solution to flow from the inlet to the outlet of the channel, at various pressures ($P_{23} + P_{24}$) and pressure differences ($\Delta P = P_{23} - P_{24}$), the latter controlling the flowrate.

The allyl production line can further comprise a cooling module (41) located directly downstream of the channel outlet (32d), for cooling the reaction products of the thermolysis reaction. Any cooling means known in the art allowing the cooling of the reaction products in a short time can be applied without affecting the present invention. A cooling module is not mandatory, but is advantageous in case an in-line analysis module (51), such as an IR spectrometer, and the like, is provided for identifying the components flowing out of the channel. Such in-line analysis modules may not be sufficiently temperature resistant to allow the reactants to flow through it without first being cooled.

A separating module (61) located downstream of the outlet for separating at least one allyl compound (3a, 3b) from other thermolysis products such as $CO_2$ and alcohols (cf. FIG. 4). The separating module can be in-line or off-line with respect of the channel (32). The separation step may comprise neutralization, liquid-liquid extraction, liquid-liquid separation, gas-liquid separation, filtration on silica gel, in-line distillation and the like. In some embodiments, liquid-liquid extraction requires the injection of a secondary phase, such as an aqueous phase. The aqueous phase may contain an inorganic salt such as sodium carbonate. Alternatively, in-line liquid-liquid or gas-liquid separation can be carried out with a membrane or a settling tank. In some embodiments, the liquid-liquid separation and the gas-liquid separation can be effected at the same time.

Allyl Formation by Thermolysis of Glycerol and Carboxylic Acid

An allyl production line as discussed supra can be used for carrying out a continuous flow process according to the present invention for the production of allyl compounds by deoxydehydration of glycerol. The continuous flow process comprises the following steps:

(a) Forming a reactive solution in the solution tank (22) by mixing glycerol (1) with a carboxylic acid (2);

(b) Feeding with the pump (23) the reactive solution to the inlet (32u) of the channel (32) of the thermolysis microreactor module discussed supra, (c) Exposing the reactive solution to thermolysis by driving a flow of the reactive solution along the channel from the inlet to the outlet (32d), for a thermolysis time, t, at a pressure, P, and at a thermolysis temperature, T, larger than 200° C., to form thermolysis products including at least one allyl compound; and (d) Recovering the thermolysis products at the outlet and separating the at least one allyl compound from the other thermolysis products The viscosity of the reaction solution is critical. Glycerol is quite viscous and, if used alone, would require a high pressure to flow through a capillary channel of a microreactor. By forming a reactive solution with a carboxylic acid, the viscosity is substantially reduced such that the reactive solution can flow easily through the channel. The reactive solution preferably has a viscosity, $\eta$, when it is fed to the inlet of the channel comprised between 0.003 and 1.1 Pa·s, preferably between 0.006 and 0.5 Pa·s. The viscosity is preferably lower than 0.5, more preferably lower than 0.3 Pa·s, most preferably lower than 0.2 Pa·s. The viscosity can be measured by strain-controlled rheology at a temperature of 20° C. and a shear rate of 99.8 $s^{-1}$. A strain-controlled rheometer, Model: ARES G2 from TA instruments was used, capable of performing a temperature sweep from −80° C. to 350° C., a frequency sweep from 0.0001 to 100 rad/s, with steady state measurement between 0.01 $s^{-1}$ and 2000 $s^{-1}$. Glycerol alone has a dynamic viscosity at 20° C. of about 1.4 Pa·s, which is too high to satisfactorily flow through capillary channels of diameter lower than 1000 µm. With a lower viscosity, the reaction solution can flow at a higher rate in the capillary channels requiring a lower pressure and temperature. A lower viscosity, however, may lead to a lower yield, as experienced by Sanchez et al. (Op. Cit.) by diluting glycerol in water to form a 35% aqueous solution of glycerol. Unlike Sanchez' aqueous solution, the reactive solution formed in the present invention does not reduce the yield of the reaction. This effect is unexpected and opens the door to cost-effective continuous production of allyl compounds using micro-/meso-fluidic.continuous flow reactors.

Figure 5:
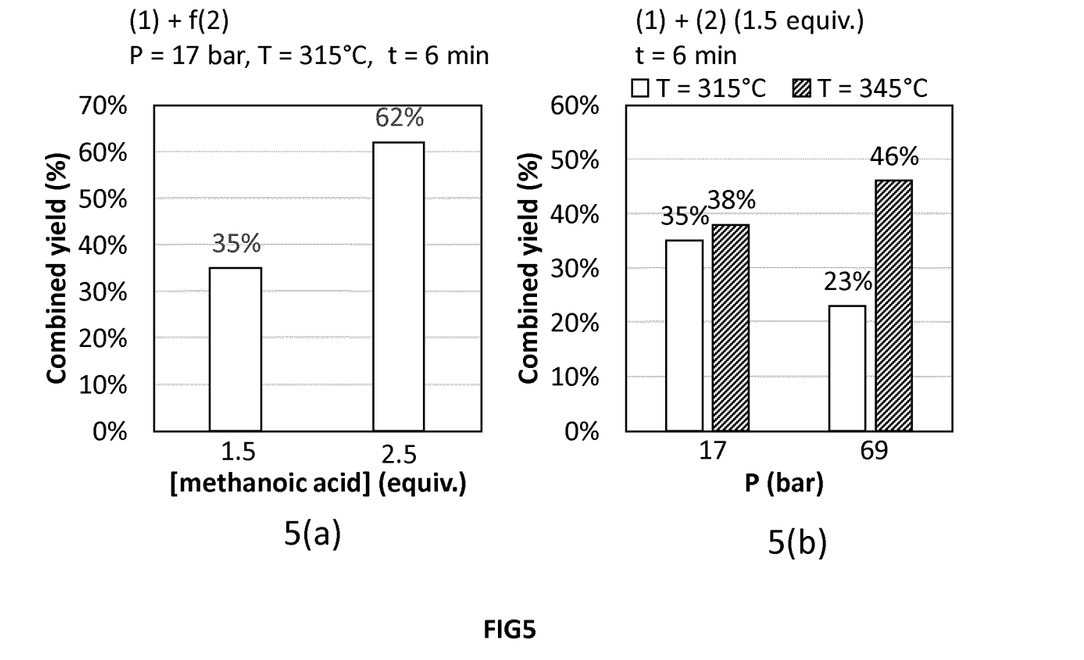
FIG. 5: illustrates the combined yields of allyl alcohol and allyl formate obtained with a process according to the present invention, combining glycerol and methanoic acid at a pressure, P, a thermolysis temperature, T, and for a thermolysis time, t=6 min (a) as a function of methanoic acid concentration at T=315° C. and P=17 bar, and (b) as a function of pressure at T=315 and 345° C., with a methanoic acid contents of 1.5 equivalent.

The carboxylic acid preferably has 1 to 5 carbons and is typically methanoic acid (2m). Carboxylic acid is preferably present in the reactive solution in an amount comprised between 1 and 3 equivalents, more preferably between 1.5 and 2.5 equivalents. According to the reaction scheme illustrated in FIG. 2, the reaction formally consumes one equivalent of methanoic acid forming 4-(hydroxymethyl)-1,3-dioxolan-2-yl formate (R=H)(2a), that is decomposed into an allyl compound, water, and $CO_2$ during the DODH process. A second equivalent is involved, but theoretically regenerated during the last irreversible step, leading to allyl alcohol (3a) and allyl formate (3b). It has been observed, however, that by adding carboxylic acid in amounts higher than the stoichiometric amount, the yield increased significantly. FIG. 5(a) compares the yield in allyl compounds obtained by thermolysis of a reaction solution composed of glycerol and methanoic acid, the latter being present in concentrations of 1.5 and 2.5 equivalents. The thermolysis conditions were T=315° C., P=17 bar (=250 psi) and t=6 min. It can be seen that by increasing the methanoic acid concentration from 1.5 to 2.5 equiv the yield jumped from 35 to 62%.

As well known by a person of ordinary skill in the art of reaction stoichiometry, a concentration expressed in "equivalent" refers to the amount of one compound (e.g., methanoic acid) that reacts with one mole of another compound (here glycerol). "Equivalent" as used herein refers to a ratio for an amount of one compound relative to 1 mol of glycerol. For example, 2 equivalents mean twice as many moles of a component as moles of glycerol. Similarly, 0.1 equivalent means ten times less moles of a compound than moles of glycerol. It follows that for 1 mole of glycerol, 2 equivalents of methanoic acid correspond to 2 moles, and 0.1 equivalent of methanoic acid corresponds to 0.1 mole.

Pressure, P, in the channel is controlled by the pressure, $P_{23}$, developed by the pump (23) and the back-pressure, $P_{24}$, developed by the backpressure regulator (BPR) (24). The pressure, P, preferably ranges between 10 and 75 bar (=145-1088 psi), preferably between 13 and 25 bar (=189 to 363 psi), more preferably between 14 to 20 bar (=203 to 290 psi), most preferably at a pressure of 17±2 bar (=250±29 psi). FIG. 5(b), illustrates the combined yield in allyl alcohol and allyl formate obtained by thermolysis of a reactive solution composed of glycerol and 1.5 equiv. methanoic acid, during a thermolysis time, t=6 min at pressures, P, of 17 and 69 bar at thermolysis temperatures, T, of 315° C. and 345° C. It can be seen that at the lower temperature, T=315° C., increasing the pressure, P, is detrimental to the conversion rate, whilst at the higher temperature, T=345° C., the opposite effect is observed.

The pressure, P, has two counterbalancing effects on the reaction outcome, since both the DODH reaction and the thermal decomposition of methanoic acid have a large positive entropy of activation. At high operating pressure, both the desired DODH reaction and the undesired thermal decomposition of methanoic acid are hindered. A series of experiments at various pressures decreasing from 69 bar to 34 bar, and further down to 17 bar (1000, 500 and 250 psi), while keeping all other process parameters constant (T=345° C., 1.5 equiv. methanoic acid, and t=6 min), led to a decrease of the conversion from 46 to 38%. Decreasing the pressure had a beneficial effect, however, when combined with a decrease of the temperature: at 315° C. the combined yield increased from 23% at a pressure, P=69 bar (=1000 psi) to 35% at a pressure, P=17 bar (250 psi), (cf. FIG. 5(b)). The thermolysis time, t, is preferably comprised between 0.1 and 15 min, preferably between 5 and 8 min. Increasing the residence time up to 30 min had no significant effect on the conversion of glycerol.

Figure 6:
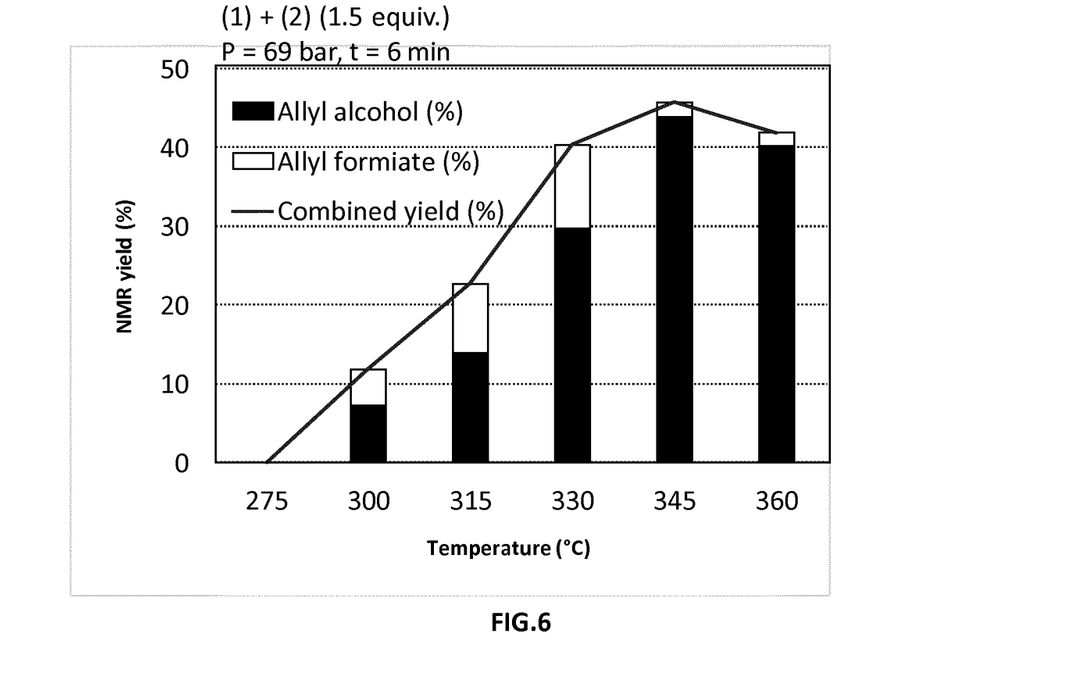
FIG. 6: illustrates the yields of allyl alcohol and allyl formate as a function of thermolysis temperature, T, obtained with a process according to the present invention, combining glycerol and methanoic acid (1.5 equiv.), at a pressure, P=69 bar, and for a thermolysis time, t=6 min.

The thermolysis temperature, T, is preferably comprised between 200 and 370° C., more preferably between 200 and 350° C. FIG. 6 illustrates the allyl alcohol and allyl formate conversion by thermolysis of a reactive solution composed of glycerol and 1.5 equiv. methanoic acid, at a pressure of 69 bar (=1000 psi) and for a thermolysis time, t=6 min as a function of thermolysis temperature, T. Increasing the residence time higher than 15 min, e.g., up to 30 min, had no significant effect on the conversion of glycerol. The 3a/3b ratio defined as the relative content of allyl alcohol with respect to the total content of allyl compounds present in the thermolysis products (=allyl alcohol/(allyl alcohol+allyl formate)) depends on the temperature, and decreases as the temperature increases ranging from 60:40 at 300° C. to 96:4 at 360° C. The increasing 3a/3b ratio at higher temperature was correlated to the thermal instability of allyl formate, forming $CO_2$ and propene above 350° C. With the thermolysis conditions used in the experiments illustrated in FIG. 6, the best conversion was obtained at a thermolysis temperature T=345° C. with a combined yield of allyl alcohol and allyl formate of 46%, and with a 3a/3b ratio of 96:4. Note that when ethanoic acid was used instead of methanoic acid, no allyl acetate was detected, therefore characterized by a 3a/3b ratio of 100:0.

Although water is not involved in the irreversible thermolysis step (cf. FIG. 2), the moisture content definitively affects the preliminary reversible steps, especially in a closed system such as in microfluidic reactors. Since the thermal decomposition of methanoic acid releases water, it has a deleterious impact on the overall DODH process as well. Reducing the moisture contents of the reactants of the reactive solution is therefore advantageous for the conversion rate of the DODH.

Allyl Formation by Thermolysis of Glycerol and a Triethyl Orthoester

Figure 3:
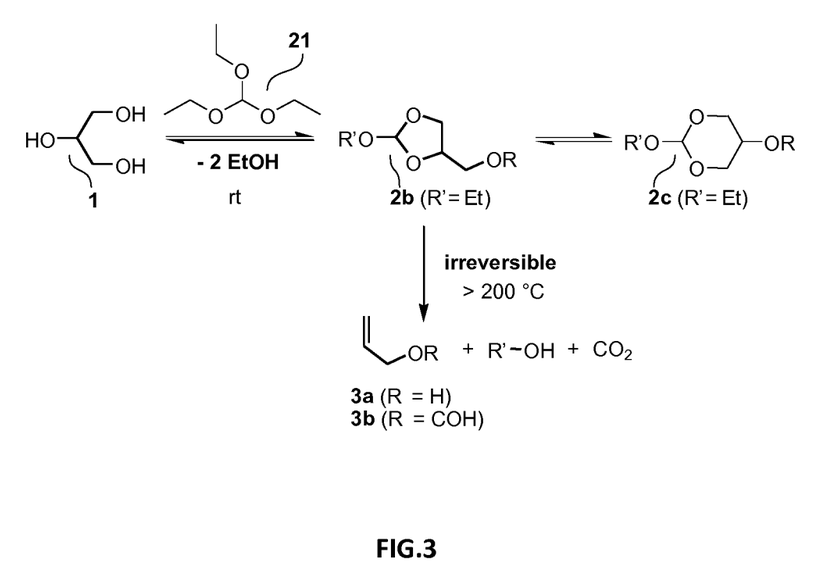
FIG. 3: shows the DODH reaction of glycerol with triethyl orthoformate.

An allyl production line as discussed supra can be used for carrying out a continuous flow process according to the present invention for the production of allyl compounds by deoxydehydration of glycerol. The continuous flow process comprises the following steps:
 (a) forming a reactive solution in the solution tank (22) by mixing glycerol (1) with a triethyl orthoester (121), preferably triethyl orthoformate (TEOF),
 (b) feeding with the pump (23) the reactive solution to the inlet (32*u*) of the channel (32) of the thermolysis microreactor module discussed supra,
 (c) exposing the reactive solution to thermolysis by driving a flow of the reactive solution along the channel from the inlet to the outlet (32*d*), for a thermolysis time, t, at a pressure, P, and at a thermolysis temperature, T, larger than 200° C., to form thermolysis products including at least one allyl compound; and
 (d) recovering the thermolysis products at the outlet and separating the at least one allyl compound from the other thermolysis products As shown in FIG. 3, glycerol and triethyl orthoester (1 equiv.) form a homogeneous reactive solution as a consequence of the dynamic covalent exchange of orthoesters leading to a 9:1 mixture of (2-ethoxy-1,3-dioxolan-4-yl) methanol (R=H) (2*b*) (hereinafter referred to as dioxolane) and 2-ethoxy-1,3-dioxan-5-ol (R=H) (2*c*) (hereinafter referred to as dioxane), as well as ethanol (EtOH). Only dioxolane (2*b*) leads to allyl alcohol through $CO_2$ extrusion. The same reactive solution could be utilized over several days without alteration of the results. The continuous-flow thermolysis of dioxolane (2*b*) in the reactive solution prepared by mixing glycerol (1) in the presence of triethyl orthoformate (21) undergoes a thermal concerted carbon dioxide elimination and hydrogen transfer to yield allyl alcohol (cf. FIG. 3).

According to the reaction scheme illustrated in FIG. 3, the reaction with glycerol (1) formally consumes one equivalent of triethyl orthoformate (TEOF) (21) that forms dioxolane (2*b*) which is decomposed into allyl alcohol (3*a*) and possibly allyl formate (3*b*), $CO_2$, and an alcohol, during the DODH process. It has been observed, however, that by adding triethyl orthoester (21) in amounts higher than the stoichiometric amount, the yield increased significantly. The triethyl orthoester is preferably present in the reactive solution in an amount comprised between 1 and 3 equivalents, more preferably between 1.5 and 2.5 equivalents.

The release of ethanol significantly reduces the viscosity of the reactive solution, and pumping can be carried out without any issues with a standard HPLC pump without any solvent. As was the case with a reactive solution composed of glycerol and a carboxylic acid, discussed supra, the reactive solution preferably has a viscosity, when it is fed to the inlet of the channel comprised between 0.003 and 1.1 Pa·s, measured as described supra Thermolysis of a reactive solution obtained by mixing glycerol and an orthoester, preferably TEOF, is preferably carried out with the following conditions. The pressure, P, is preferably comprised between 10-75 bar (=145-1088 psi), more preferably between 13 and 25 bar (=189 to 363 psi), more preferably between 14 to 20 bar (=203 to 290 psi), and most preferably at a pressure of 17±2 bar (=250±29 psi). The thermolysis time, t, is preferably comprised between 0.1 and 15 min, preferably between 5 and 8 min. Increasing the residence time up to 30 min had no significant effect on the conversion of glycerol. The thermolysis temperature, T, is preferably comprised between 200 and 370° C., preferably between 220 and 320° C.

The absence of solvent, and the unique profile of the reagents and products enables convenient monitoring of the reaction course using in-line IR spectroscopy (51) (cf. FIG. 4). The appearance of allyl alcohol (3*a*) (vc=c at 1648 cm$^{-1}$) and allyl formate (3*b*) (vc=c at 1656 cm$^{-1}$ and vc=o at 1730 cm$^{-1}$) was monitored through the evolution of the main characteristic vibration bands. In-line conversion of glycerol to (3*a*,3*b*) were obtained by combining in-line IR qualitative information and off-line quantitative NMR. The evolution of the intensity of the characteristic vibration band (vc=o at 2340 cm$^{-1}$) of dissolved $CO_2$ can be correlated to the conversion of glycerol. The white squares in FIG. 7(*a*) illustrate the yield of allyl compounds as a function of temperature for a reactive solution obtained by mixing glycerol (1) and 1 equivalent TEOF (21). The pressure, P, in the channel was 17 bar and the thermolysis time was 6 min. The reaction started at 175° C. and reached 5% after 6 min residence time. Rising the temperature up to 300° C. increased up to 27% the formation of allyl alcohol (3*a*). The conversion reached 55% at 350° C., but some clogging was observed. Allyl formate (3*b*) was not observed under these conditions.

Figure 7:
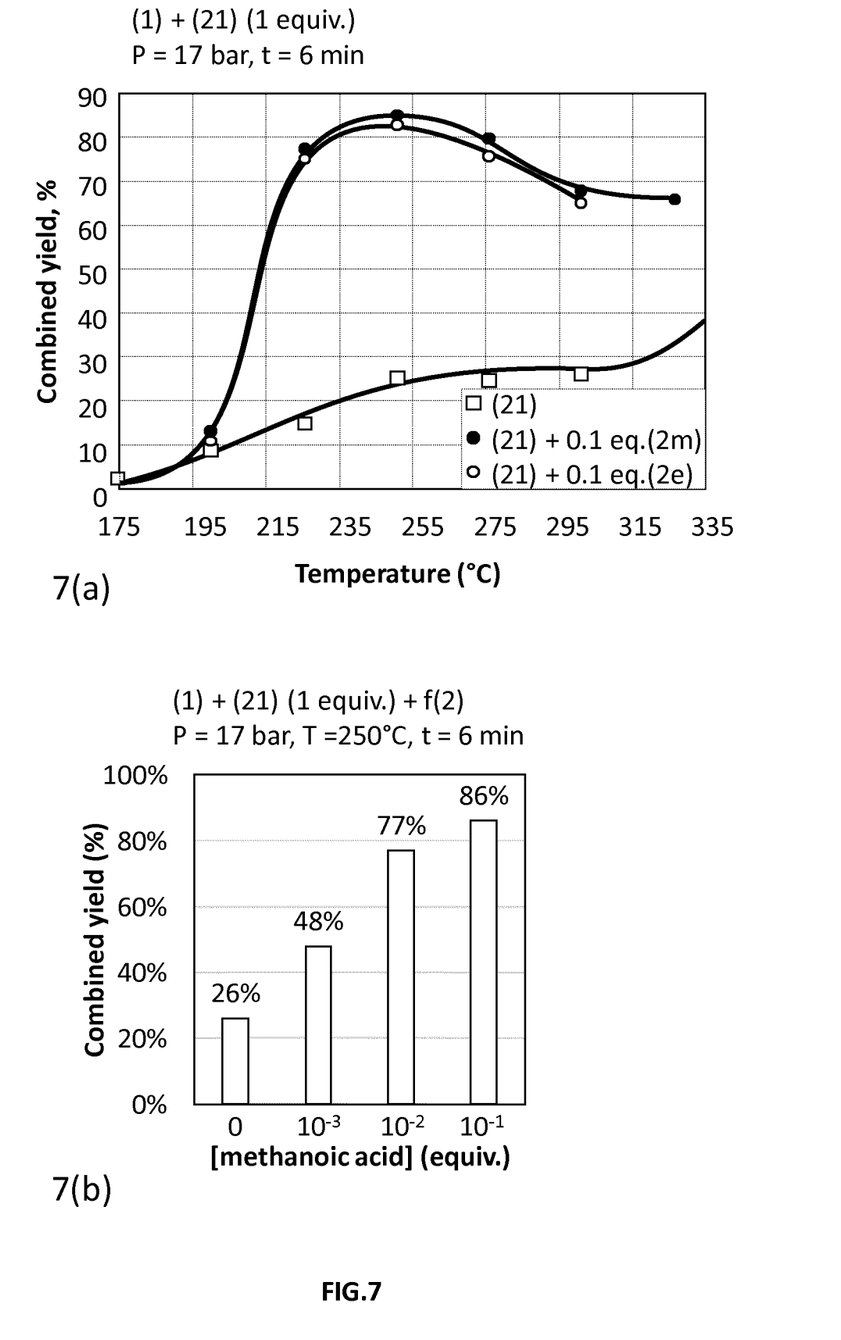
FIG. 7: illustrates the combined yields of allyl alcohol and allyl formate (a) as a function of thermolysis temperature, T, and (b) as a function of carboxylic acid concentration, obtained with a process according to the present invention carried out at a pressure, P=17 bar, and for a thermolysis time, t=6 min of a reactive solution obtained by mixing glycerol and TEOF (1 equiv.) used alone (white squares), or together with 1 equiv. of a carboxylic acid: white circles=ethanoic acid, and black circles=methanoic acid.

Allyl Formation by Thermolysis of Glycerol, a Carboxylic Acid, and a Triethyl Orthoester An allyl production line as discussed supra can be used for carrying out a continuous flow process according to the present invention for the production of allyl compounds by deoxydehydration of glycerol. The continuous flow process comprises the following steps:

(a) Forming a reactive solution in the solution tank (22) by mixing:
glycerol (1) with,
carboxylic acid (2), and with,
a triethyl orthoester (121), preferably triethyl orthoformate (TEOF),
(b) feeding with the pump (23) the reactive solution to the inlet (32u) of the channel (32) of the thermolysis microreactor module discussed supra,
(c) exposing the reactive solution to thermolysis by driving a flow of the reactive solution along the channel from the inlet to the outlet (32d), for a thermolysis time, t, at a pressure, P, and at a thermolysis temperature, T, larger than 200° C., to form thermolysis products including at least one allyl compound; and
(d) recovering the thermolysis products at the outlet and separating the at least one allyl compound from the other thermolysis products As discussed supra in reference with FIG. 7(a), DODH of glycerol and triethyl orthoester, in particular TEOF, yields a moderate conversion rate into allyl alcohol of 27% at 315° C. Adding a carboxylic acid to the reactive solution of glycerol and TEOF, did not trigger any significant conversion rate differences at thermolysis temperatures of up to 200° C. As shown in FIG. 7(a), however, a huge difference was noticed at temperatures higher than 225° C. The black and white circles in FIG. 7(a) indicate the yield in allyl compounds by DODH of glycerol and TEOF with 0.1 equivalent of methanoic and ethanoic acid, respectively.

The presence of a carboxylic acid, even in low amounts of between $10^{-3}$ to $10^{-1}$ equivalent (=0.1 to 10 mol % for 1 mol of glycerol) yielded a substantial increase of the yield in allyl compounds of up to nearly 90% at 250° C. No significant effect, however, of the nature of the carboxylic acid could be identified between methanoic acid (2m) and ethanoic acid (2e). With both acids, the yield decreased above 250° C. No allyl acetate was formed when ethanoic acid was used. As shown in FIG. 7(b), in the presence of a increasing amount of methanoic acid from $10^{-3}$ to $10^{-2}$, and to $10^{-1}$ equivalent (=0.1 to 1, and to 10 mol %), the yield at 250° C. and 6 min thermolysis time increased from 26% without carboxylic acid, to 48%, up to 77%, and to 86%, respectively. The system with $10^{-1}$ equivalent methanoic acid (black circles) at 250° C. yielded a 3a/3b ratio of 98:2 and was operated for 12 h in a row without any decrease in performance. Most importantly, it provided consistent results over various production campaigns even with aged glycerol samples.

Thermolysis of a reactive solution obtained by mixing glycerol (1), a carboxylic acid (2), and a triethyl orthoester (21) is preferably carried out at a pressure, P, comprised between 10 and 75 bar (=145-1088 psi), more preferably between 13 and 25 bar (=189 to 363 psi), more preferably between 14 to 20 bar (=203 to 290 psi), and most preferably at a pressure of 17±2 bar (=250±29 psi). The thermolysis time, t, is preferably comprised between 0.1 and 15 min, preferably between 5 and 8 min. Increasing the residence time up to 30 min had no significant effect on the conversion of glycerol. The thermolysis temperature, T, is preferably comprised between 200 and 370° C., preferably between 220 and 320° C.

According to the reaction scheme illustrated in FIG. 3, one equivalent of triethyl orthoformate (TEOF) (21) forming one equivalent of dioxolane (2b) suffices to form an allyl compound (3a, 3b). The triethyl orthoester is preferably present in the reactive solution in an amount comprised between 1 and 3 equivalents, more preferably between 1.5 and 2.5 equivalents, as it has been observed, that the yield increased with higher amounts of triethyl orthoester (21).

The carboxylic acid (2) can be present in the reactive solution in an amount comprised between 0.001 and 1.5 equivalent, preferably between 0.01 and 1 equivalent. As discussed in continuation, the amount of carboxylic acid can be increased to 3 equivalents when used together with a triethyl orthoester.

Figure 8:
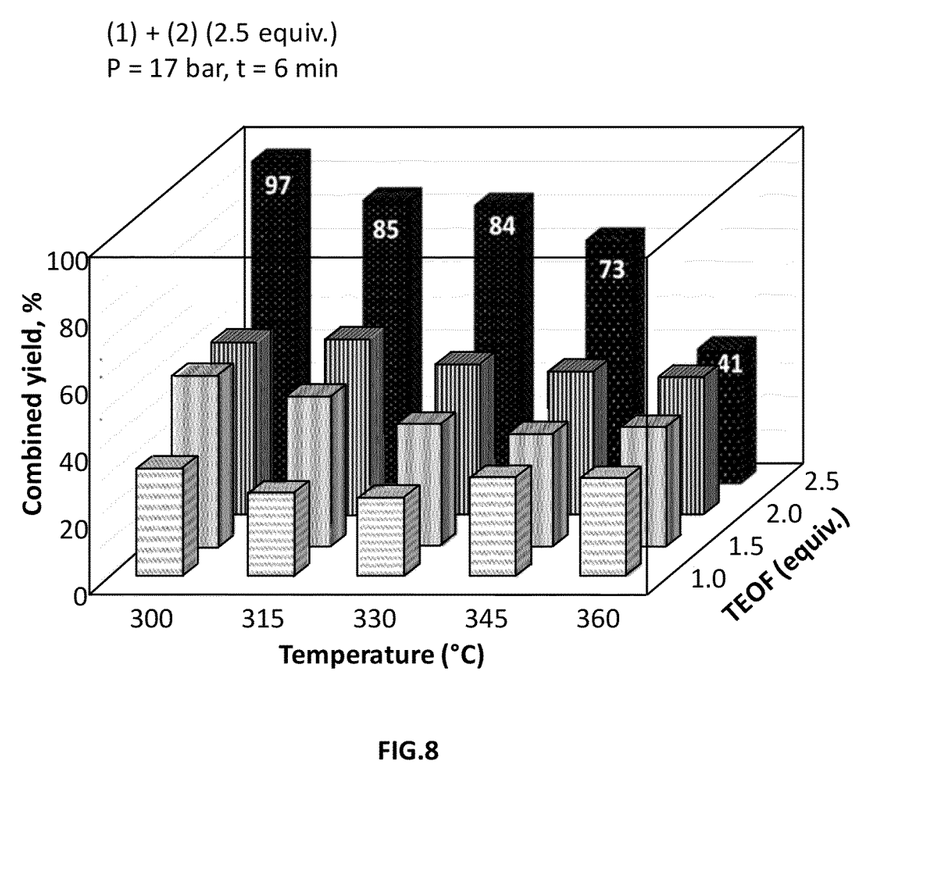
FIG. 8: illustrates the combined yield of allyl alcohol and allyl formate as a function of thermolysis temperature, T, and contents of triethyl orthoformate (TEOF) obtained with a process according to the present invention, combining glycerol, methanoic acid (2.5 equiv.), and various concentrations of triethyl orthoformate, at a pressure, P=17 bar, and for a thermolysis time, t=6 min

As discussed supra and illustrated in FIG. 7(b), a carboxylic acid can be present in small amounts, such as $10^{-3}$ to $10^{-1}$ equivalent (=0.1 to 10 mol % for 1 mol of glycerol) and increase the conversion rate of allyl compounds from 26% with no carboxylic acid to 47%, 77%, and up to 86% by addition of $10^{-3}$, $10^{-1}$, and $10^{-1}$ equivalent of methanoic acid, respectively. By further increasing the amount of carboxylic acid to 2.5 or 3 equivalents, yet higher conversion rates can be achieved. When used alone (i.e., in the absence of TEOF), it is preferred that the carboxylic acid be present in an amount higher than 2 equivalents. FIG. 8 illustrates the combined yield of allyl compounds (3a, 3b) obtained by thermolysis at a pressure, P=17 bar, for a thermolysis time, t=6 min; of a reactive solution obtained by mixing glycerol (1), 2.5 equivalents of carboxylic (methanoic) acid (2), and various amounts of TEOF ranging between 1 and 2.5 equivalents.

It can be seen in FIG. 8 that for all temperatures, the conversion rate increases with higher amounts of TEOF. The highest conversion rate of 97% was obtained with 2.5 equivalents of methanoic acid and 2.5 equivalents of TEOF at a thermolysis temperature, T=300° C. Accordingly, in a preferred embodiment of the present invention, the reactive solution comprises both triethyl orthoformate (TEOF) and a carboxylic acid, present in amounts which do not differ from one another by more than ±20%, said amounts being preferably comprised between 2 and 3 equivalents, preferably between 2.3 and 2.7 equivalents, and wherein the thermolysis temperature is comprised between 200 and 370° C., preferably between 220 and 345° C., more preferably between 270 and 320° C.

According to the reaction scheme illustrated in FIG. 3, the reaction between glycerol (1) and triethyl orthoformate (TEOF) (21) forms dioxolane (2b), dioxane (2c), and ethanol. The release of ethanol significantly reduces the viscosity of the reactive solution, and pumping can be carried out without any issues with a standard HPLC pump without any solvent. As was the case with a reactive solution composed of glycerol and a carboxylic acid, discussed supra, the reactive solution preferably has a viscosity, η, when it is fed to the inlet of the channel comprised between 0.003 and 1.1 Pa·s, measured as described supra.

EXAMPLES

The following Examples were carried out to illustrate the present invention. Table 1 summarizes the performances measured for Examples.

Example 1

Continuous-Flow DODH of Glycerol (1) with Methanoic Acid (2m)

A dynamic reactive solution of glycerol was prepared by mixing glycerol (1) and 1.5 equiv. of methanoic acid (2m) (200 ml total volume), and connected to a HPLC pump (23) set at 0.12 ml min$^{-1}$. The reactive feed solution was then thermolyzed at 345° C. at a pressure, P=69 bar (=1000 psi) of counter pressure in a production line as illustrated in FIG. 4. The outlet (32*d*) of the reaction coil was connected to a cooling SS capillary loop (41) (0.34 ml internal volume, 2.8 min residence time). The outlet of the second SS loop was connected to an in-line IR spectrometer (51), and a 17 bar (=250 psi) backpressure regulator (24) (BPR) was inserted downstream, for a thermolysis time, t=6 min. The reactor effluent was collected and analyzed by $^1$H NMR yielding 46% combined yield, with a 96:4 3*a*/3*b* selectivity.

Example 2

Continuous-Flow DODH of Glycerol (1) with Methanoic Acid (2*m*)

The same set up as described in Example 1 was used, pumping a dynamic reactive solution of glycerol (1) and 2.5 equiv. of methanoic acid (2*m*) (200 ml total volume). The reactive mixture was thermolyzed at T=315° C. at a pressure, P=17 bar (=250 psi) of counter pressure in a production line as illustrated in FIG. 4. The thermolysis time, t, was 13 min. The reactor effluent was collected and analyzed by $^1$H NMR, yielding 62% combined yield with a 90:10 3*a*/3*b* selectivity.

Example 3

Continuous-Flow DODH with Triethyl Orthoformate

The same set up as described in Example 1 was used, pumping a dynamic reactive solution of glycerol prepared by mixing glycerol (1) and 1 equiv. of triethyl orthoformate (21) (200 ml total volume). The HPLC pump used to deliver the dynamic reactive feed solution of glycerol was set at 0.26 ml min$^{-1}$. The reactive mixture was thermolyzed at T=250° C. at a pressure, P=17 bar (=250 psi) of counter pressure in a production line as illustrated in FIG. 4. The thermolysis time, t, was 6 min. The reactor effluent was collected and analyzed by $^1$H NMR yielding 26% combined yield with a 100:0 3*a*/3*b* ratio.

Example 4

Continuous-Flow DODH with Triethyl Orthoformate

The same set up as described in Example 5 was used, pumping a dynamic reactive solution of glycerol prepared by mixing glycerol (1) and 1 equiv. of triethyl orthoformate (21) (200 ml total volume). The HPLC pump used to deliver the dynamic reactive feed solution of glycerol was set at 0.26 ml min$^{-1}$. The reactive mixture was thermolyzed at T=350° C. at a pressure, P=17 bar (=250 psi) of counter pressure in a production line as illustrated in FIG. 4. The thermolysis time, t, was 6 min. The reactor effluent was collected and analyzed by $^1$H NMR yielding 55% combined yield with a 100:0 3*a*/3*b* ratio. Some clogging was, however, observed.

Example 5

Continuous-Flow DODH with 1 eq. Triethyl Orthoformate (21) and 10$^{-3}$ eq. Methanoic Acid (2*m*)

The same set up as described in Example 1 was used, pumping a dynamic reactive solution of glycerol prepared by mixing glycerol (1), 1 equiv. of triethyl orthoformate (21) and 10$^{-3}$ equivalent of methanoic acid (2*m*) (=0.1 mol %) (200 ml total volume). The HPLC pump used to deliver the dynamic reactive feed solution of glycerol was set at 0.26 ml min$^{-1}$. The reactive mixture was thermolyzed at T=250° C. at a pressure, P=17 bar (=250 psi) of counter pressure in a production line as illustrated in FIG. 4. The thermolysis time, t, was 6 min. The reactor effluent was collected and analyzed by $^1$H NMR yielding 48% combined yield with a 99:1 3*a*/3*b* ratio Example 6

Continuous-Flow DODH with 1 eq. Triethyl Orthoformate (21) and 10$^{-2}$ eq. Methanoic Acid (2*m*)

The same set up as described in Example 1 was used, pumping a dynamic reactive solution of glycerol prepared by mixing glycerol (1), 1 equiv. of triethyl orthoformate (21) and 10$^{-2}$ equivalent of methanoic acid (2*m*) (=1 mol %) (200 ml total volume). The HPLC pump used to deliver the dynamic reactive feed solution of glycerol was set at 0.26 ml min$^{-1}$. The reactive mixture was thermolyzed at T=250° C. at a pressure, P=17 bar (=250 psi) of counter pressure in a production line as illustrated in FIG. 4. The thermolysis time, t, was 6 min. The reactor effluent was collected and analyzed by $^1$H NMR yielding 77% combined yield with a 99:1 3*a*/3*b* ratio Example 7

Continuous-Flow DODH with 1 eq. Triethyl Orthoformate (21) and 10$^{-1}$ eq. Methanoic Acid (2*m*)

The same set up as described in Example 1 was used, pumping a dynamic reactive solution of glycerol prepared by mixing glycerol (1), 1 equiv. of triethyl orthoformate (21) and 10$^{-1}$ equivalent of methanoic acid (2*m*) (=10 mol %) (200 ml total volume). The HPLC pump used to deliver the dynamic reactive feed solution of glycerol was set at 0.26 ml min$^{-1}$. The reactive mixture was thermolyzed at T=250° C. at a pressure, P=17 bar (=250 psi) of counter pressure in a production line as illustrated in FIG. 4. The thermolysis time, t, was 6 min. The reactor effluent was collected and analyzed by $^1$H NMR yielding 86% combined yield with a 99:1 3*a*/3*b* ratio Example 8

Continuous-Flow DODH with 1 eq. Triethyl Orthoformate (21) and 10$^{-1}$ eq. Ethanoic Acid (2*e*)

The same set up as described in Example 8 was used, pumping a dynamic reactive solution of glycerol prepared by mixing glycerol (1), 1 equiv. of triethyl orthoformate (21) and 10$^{-1}$ equivalent of ethanoic acid (2*e*) (=10 mol %) (200 ml total volume). The HPLC pump used to deliver the dynamic reactive feed solution of glycerol was set at 0.26 ml min$^{-1}$. The reactive mixture was thermolyzed at T=250° C. at a pressure, P=17 bar (=250 psi) of counter pressure in a production line as illustrated in FIG. 4. The thermolysis time, t, was 6 min. The reactor effluent was collected and analyzed by $^1$H NMR yielding 84% combined yield with a 99:1 3*a*/3*b* ratio.

Example 9

Continuous-Flow DODH with 2.5 eq. Triethyl Orthoformate (21) and 2.5 eq. Methanoic Acid (2m)

The same set up as described in Example 1 was used, pumping a dynamic reactive solution of glycerol prepared by mixing glycerol (1), 2.5 equiv. of methanoic acid (2m), and 2.5 equiv. of triethyl orthoformate (21) (200 ml total volume). The reactive mixture was thermolyzed at T=300° C. at a pressure, P=17 bar (=250 psi) of counter pressure in a production line as illustrated in FIG. 4. The thermolysis time, t, was 1 min. The reactor effluent was collected and analyzed by $^1$H NMR, yielding 85% combined yield with a 90:10 3a/3b selectivity.

| | Glycerol mol | methan. ac. eq. | TEOF eq. | T °C. | P Psi (bar) | t min | yield % | 3a/3b — |
|---|---|---|---|---|---|---|---|---|
| Ex. 1 | 1 | 1.5 | 0 | 345 | 1000 (69.4) | 6 | 46% | 96/4 |
| Ex. 2 | 1 | 2.5 | 0 | 315 | 250 (17.2) | 13 | 62% | 90/10 |
| Ex. 3 | 1 | 0 | 1 | 250 | 250 (17.2) | 6 | 26% | 100/0 |
| Ex. 4 | 1 | 0 | 1 | 350 | 250 (17.2) | 6 | 55% | 100/0 |
| Ex. 5 | 1 | 0.001 | 1 | 250 | 250 (17.2) | 6 | 48% | 99/1 |
| Ex. 6 | 1 | 0.01 | 1 | 250 | 250 (17.2) | 6 | 77% | 99/1 |
| Ex. 7 | 1 | 0.1 | 1 | 250 | 250 (17.2) | 6 | 86% | 99/1 |
| Ex. 8* | 1 | 0.1 | 1 | 250 | 250 (17.2) | 6 | 84% | 99/1 |
| Ex. 9 | 1 | 2.5 | 2.5 | 300 | 250 (17.2) | 1 | 85% | 90/10 |
| Ex. 10 | 1 | 2.5 | 2.5 | 300 | 250 (17.2) | 6 | 97% | 80/20 |

*ethanoic acid was used instead of methanoic acid.

Example 10

Continuous-Flow DODH with 2.5 eq. Triethyl Orthoformate (21) and 2.5 eq. Methanoic Acid (2m)

The same set up as described in Example 3 was used, pumping a dynamic reactive solution of glycerol prepared by mixing glycerol (1), 2.5 equiv. of methanoic acid (2m), and 2.5 equiv. of triethyl orthoformate (21) (200 ml total volume). The reactive mixture was thermolyzed at T=300° C. at a pressure, P=17 bar (=250 psi) of counter pressure in a production line as illustrated in FIG. 4. The thermolysis time, t, was 6 min. The reactor effluent was collected and analyzed by $^1$H NMR yielding 97% combined yield with an 80:20 3a/3b ratio.

The present invention implements the DODH reaction of glycerol under continuous-flow conditions in a microfluidic reactor setup. Dynamic reactive solutions are produced by mixing glycerol with a carboxylic acid (2), a triethyl orthoester (21), or a combination of both. Quick exposure to elevated temperatures under moderate pressure ensure short reaction times of less than 15 min, high yield of up to 97%, and excellent control of the selectivity. Triethyl orthoformate is a preferred triethyl orthoester. Best results are obtained when using triethyl orthoformate together with an amount of carboxylic acid for the DODH of glycerol, with shorter reaction times and lower reaction temperatures and high yields. The continuous flow process of the present invention is robust and gives reproducible results even with bio-sourced glycerol.

| # | feature |
|---|---|
| 1 | glycerol |
| 2 | carboxylic acid |
| 2a | 4-(hydroxymethyl)-1,3-dioxolan-2-yl formate (R = H) |
| 2b | (2-ethoxy-1,3-dioxolan-4-yl)methanol (R = H) (=dioxolane) |
| 2c | ethoxy-1,3-dioxan-5-ol (R = H) (=dioxane) |
| 2e | ethanoic acid |
| 2m | methanoic acid |
| 3a | allyl alcohol |
| 3b | allyl formate |
| 11 | source of glycerol |
| 12 | source of carboxylic acid |
| 21 | triethyl orthoester (e.g., TEOF) |
| 22 | solution tank |
| 23 | pump |
| 24 | backpressure regulator (BPR) |

-continued

| # | feature |
|---|---|
| 31 | thermolysis microreactor module |
| 32 | channel |
| 32d | channel outlet |
| 32u | channel inlet |
| 41 | cooling module |
| 51 | in-line analysis module |
| 61 | separating module |
| 121 | source of triethyl orthoester |

The invention claimed is:
1. A continuous-flow process for the production of allyl compounds by deoxydehydration of glycerol comprising:
  (a) forming a reactive solution by mixing glycerol (1) with:
    a carboxylic acid (2), or
    a triethyl orthoester, preferably triethyl orthoformate (TEOF), or a combination thereof, with the proviso that when used alone, the carboxylic acid (2) is present in the reactive solution in an amount of at least 2 equivalents;
  (b) feeding the reactive solution to an inlet of a channel of a thermolysis microreactor module wherein the channel has an inner hydraulic diameter, D=4 A/P, wherein A is the area and P the perimeter of a cross-section of the channel, of not more than 1000 μm,
  (c) exposing the reactive solution to thermolysis by driving a flow of the reactive solution along the channel from the inlet to an outlet, for a thermolysis time, t, at a pressure, P, and at a thermolysis temperature, T, larger than 200° C., to form thermolysis products including at least one allyl compound; and (d) recovering the thermolysis products at the outlet and separating the at least one allyl compound from the other thermolysis products.

2. The continuous-flow process according to claim 1, wherein,
the triethyl orthoester is present in the reactive solution in an amount comprised between 1 and 3 equivalents, or
the carboxylic acid (2) is present in the reactive solution in an amount comprised between 1 and 3 equivalents, or a combination thereof.

3. The continuous-flow process according to claim 1, wherein,
the triethyl orthoester is present in the reactive solution in an amount comprised between 1 and 3 equivalents, and
the carboxylic acid (2) is present in the reactive solution in an amount comprised between 0.001 and 1.5 equivalents.

4. The continuous-flow process according to claim 1, wherein the at least one allyl compound present in the thermolysis products comprises allyl alcohol and allyl formate, wherein the 3a/3b ratio defined as the relative content of allyl alcohol with respect to the total content of allyl compounds present in the thermolysis products (=allyl alcohol/(allyl alcohol+allyl formate)) is comprised between 50 and 100%.

5. The continuous-flow process according to claim 1, wherein the reactive solution has a viscosity, $\eta$, when it is fed to the inlet of the channel comprised between 0.003 and 1.1, wherein the viscosity is measured by strain-controlled rheology at a temperature of 20° C. and a shear rate of 99.8 $s^{-1}$.

6. The continuous-flow process according to claim 1, wherein the carboxylic acid has 1 to 5 carbons.

7. The continuous-flow process according to claim 1, wherein the thermolysis reaction is carried out at a pressure, P, comprised between 10-75 bar (=145-1088 psi).

8. The continuous-flow process according to claim 1, wherein the thermolysis temperature, T, is comprised between 200 and 370° C.

9. The continuous-flow process according to claim 1, wherein,
the reactive solution comprises both triethyl orthoformate (TEOF) and a carboxylic acid, present in amounts which do not differ from one another by more than ±20%, and wherein
the thermolysis temperature is comprised between 200 and 370° C.

10. The continuous-flow process according to claim 1, wherein the separation step comprises one or more of neutralization, liquid-liquid extraction, liquid-liquid separation, gas-liquid separation, filtration on silica gel, in-line distillation.

11. An allyl production line for carrying out the continuous flow process according to claim 1 comprising:
(a) sources of reactants including:
a source of glycerol, and
a source of a triethyl orthoester (121), preferably triethyl orthoformate (TEOF), and/or a source of carboxylic acid,
(b) a solution tank (22) in fluid communication with the sources of reactants,
(c) a pump bringing in fluid communication the solution tank with a thermolysis microreactor module, wherein
(d) the thermolysis microreactor module comprises:
a channel extending from an inlet to an outlet located downstream from the inlet, said channel having an inner hydraulic diameter, D=4 A/P, wherein A is the area and P the perimeter of a cross-section of the channel, of not more than 1000 µm, wherein the pump is located directly upstream of the inlet,
a heating module arranged for heating the channel at a thermolysis temperature of at least 200° C.,
(e) a separating module (61) located downstream of the outlet for separating at least one allyl compound from other thermolysis products.

12. The allyl production line according to claim 11, wherein the separating module comprises one or more units selected among neutralization unit, liquid-liquid extraction unit, liquid-liquid separation unit, gas-liquid separation unit, filtration on silica gel unit, in-line distillation unit.

13. The continuous-flow process according to claim 2, wherein the triethyl orthoester is present between 1.5 and 2.5 equivalents.

14. The continuous-flow process according to claim 2, wherein the triethyl orthoester is triethyl orthoformate (TEOF).

15. The continuous-flow process according to claim 2, wherein, the carboxylic acid (2) is present in the reactive solution in an amount of between 1.5 and 2.5 equivalents.

16. The continuous-flow process according to claim 2, wherein only the carboxylic acid (2) is present and in the reactive solution in an amount of at least 2 equivalents.

17. The continuous-flow process according to claim 3, wherein both the triethyl orthoester and the carboxylic acid (2) are present in the reactive solution and the carboxylic acid (2) is present between 0.01 and 1 equivalent.

18. The continuous-flow process according to claim 4, wherein the thermolysis products (=allyl alcohol/(allyl alcohol+allyl formate)) is between 75 and 99%.

19. The continuous-flow process according to claim 5, wherein the viscosity is between 0.006 and 0.5 Pa.s.

20. The continuous-flow process according to claim 6, wherein the carboxylic acid is methanoic acid (2m) or ethanoic acid (2e).

* * * * *